United States Patent [19]
Robbins et al.

[11] 4,428,379
[45] Jan. 31, 1984

[54] PASSIVE ULTRASOUND NEEDLE PROBE LOCATOR

[75] Inventors: C. Wayne Robbins, Lawrenceville; William S. N. Trimmer, Belle Mead, both of N.J.

[73] Assignee: Technicare Corporation, Solon, Ohio

[21] Appl. No.: 337,872

[22] Filed: Jan. 7, 1982

[51] Int. Cl.³ .............................................. A61B 10/00
[52] U.S. Cl. ..................... 128/660; 128/653; 73/644
[58] Field of Search .................. 128/660-663, 128/751, 754, 24 A, 653; 73/630, 632, 643-644; 433/86, 119; 310/26

[56] References Cited

U.S. PATENT DOCUMENTS

| | | | |
|---|---|---|---|
| 2,638,567 | 5/1953 | Cronin | 310/26 X |
| 2,831,132 | 4/1958 | Jackson | 310/26 |
| 3,556,079 | 1/1971 | Omizo | 128/661 |
| 3,663,842 | 5/1972 | Miller | 73/644 X |
| 3,721,227 | 3/1973 | Larson et al. | 128/660 |
| 3,890,423 | 6/1975 | Zacharias, Jr. | 73/644 X |
| 4,029,084 | 6/1977 | Soldner | 128/660 |
| 4,058,114 | 11/1977 | Soldner | 128/754 X |
| 4,108,165 | 8/1978 | Kopp et al. | 128/660 |
| 4,130,018 | 12/1978 | Adams et al. | 73/644 X |
| 4,184,094 | 1/1980 | Kopel | 128/660 X |
| 4,249,539 | 2/1981 | Vilkomerson et al. | 128/660 |

FOREIGN PATENT DOCUMENTS

| | | | |
|---|---|---|---|
| 39045 | 11/1981 | European Pat. Off. | 128/660 |
| 2455401 | 11/1974 | Fed. Rep. of Germany | 128/660 |

OTHER PUBLICATIONS

Sommer et al.; "A Phantom for Imaging Biological Fluids by Ultrasound and CT Scanning"; *Ultrasound in Med. and Biol.*; vol. 6, No. 2, 1980, pp. 135-140.

Time, Oct. 2, 1964, p. 96, "Surgery, Into the Eye with Ultrasound".

*Primary Examiner*—Lee S. Cohen
*Assistant Examiner*—Angela D. Sykes

[57] ABSTRACT

A solid steel stylette is carried coaxially within a hollow biopsy needle, with the void therebetween filled and packed with several layers of hollow plastic microspheres having an approximate diameter of 0.80 millimeters. Ultrasound energy impinging on the needle tip is converted to pressure waves which are conveyed back up the stylette, there to be converted to electrical energy for coordination with the image of the system. The packing of hollow plastic microspheres acoustically insulates the stylette from the needle.

3 Claims, 9 Drawing Figures

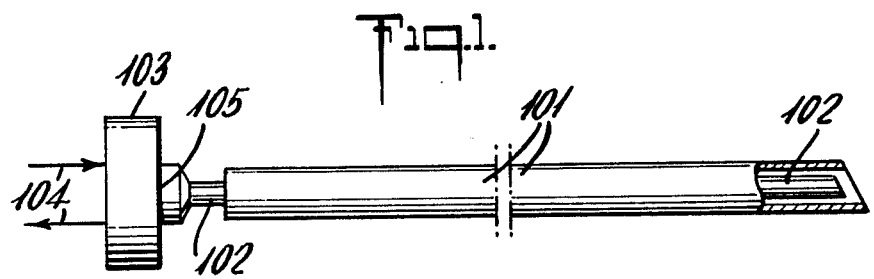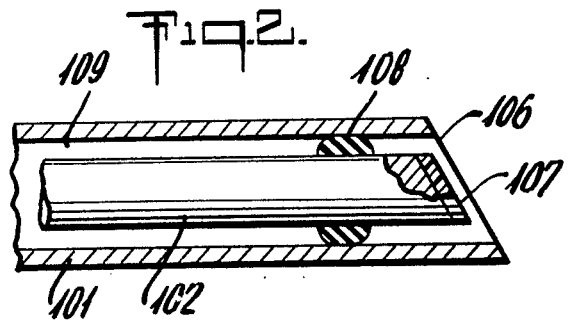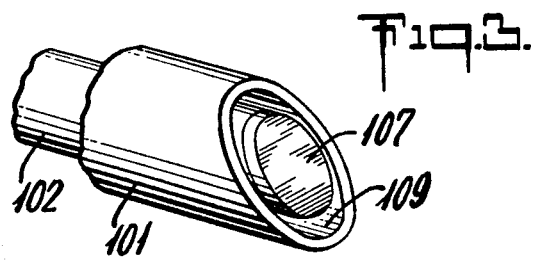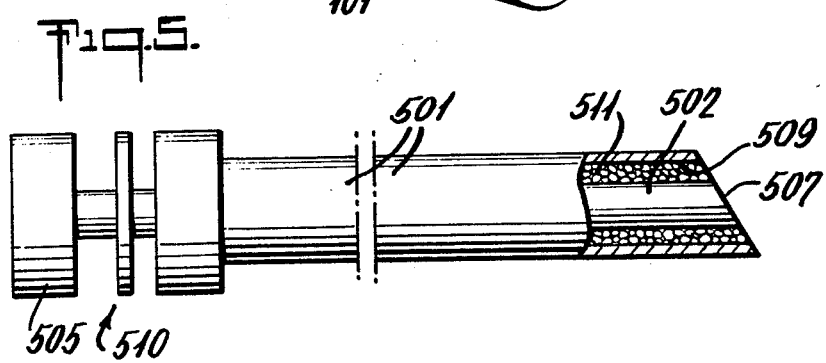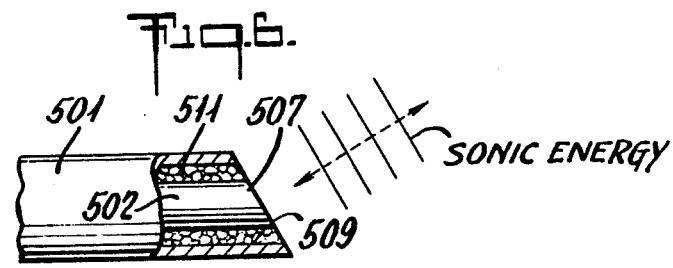

PASSIVE ULTRASOUND NEEDLE PROBE LOCATOR

FIELD OF THE INVENTION

This invention relates to ultrasound imaging systems, and more particularly to methods and apparatus for the utilization of such systems to track and control the location of needle probes within the body.

BACKGROUND OF THE INVENTION

In a copending, concurrently filed patent application of W. Trimmer et al., Ser. No. 337,899 there is described a system premised on utilization of a stylettelike passive element for sensing sonic pulses in the body, and conveying those pulses, as sonic energy, out through the needle, where they are converted to electrical energy. Thus, a cylindrical needle probe carries a coaxial conduit rod, which terminates in the region of the needle tip, as desired either just outside, at, or within the needle tip. The stylette conduit is coupled to a transducer outside the body, such that ultrasound pressure waves which are conducted through the needle and out of the body are only then converted to electrical energy. Hence, the only portions of the apparatus which penetrate and/or contact body tissues are the electrically passive, essentially disposable and easily sterilizable needle and stylette portions. In preferred embodiments, the sonic conduit is fashioned of stainless steel, and terminates in a sonic matching layer. In some embodiments, the interior surface of the needle sheath is not physically isolated from the stylette, it being understood that during insertion, some mutual bending may occur, and some incidental contact may occur between the stylette and the needle. Other embodiments, however, seek to insure that minimal acoustic energy transfer will occur between the stylette and the interior of the needle sheath. Thus, as will be particularly noted from FIGS. 7A and 7B, and FIGS. 8A and 8B of the concurrently filed copending application of Trimmer et al., annular or helical ridges, or an overall helical stylette shape create periodic points of contact between the stylette and the interior needle surface. These points of contact are, hopefully, sufficiently small in area, or oblique in angle of contact whereby the sonic pressure wave moves directly up the stylette, and is not substantially transferred to the needle sheath interior. Similarly acoustical energy from the exterior of the needle is substantially transferred to the stylette.

It is an object of the present invention to provide acoustic isolation between the sonic energy carrying stylette, and the surrounding needle in such systems. It is a more particular object of the principles of the present invention to provide the sorts of acoustical interface which avoid even point contact interface between the sonic conduit (i.e. stylette) and the surrounding hollow needle.

SUMMARY OF THE INVENTION

In accordance with the principles of the present invention, a packing of hollow, plastic microspheres substantially completely sonically isolates the stylette from the interior of the needle sheath. Hence, pressure waves originating at the stylette tip are conveyed back through the needle and to an external transducer/utilization apparatus, free of the danger of significant transfer of those pressure waves to the needle itself. In a preferred embodiment, the stylette is of stainless steel and conventional, rod-shaped construction (either finished smooth at its face or carrying a matching layer, as described by Trimmer et al.); is first coated, either by dipping or spin coating, with a low viscosity nonconductive epoxy film, and then immersed into a vessel filled with the plastic microspheres, which adhere to the epoxy. After curing of the epoxy, the stylette is inserted into the needle, thereby shearing off the excessive microspheres, and insuring a well-packed, integral acoustic insulation between the stylette and the interior of the needle.

It is a feature of the present invention that needle locator systems of the sort described and claimed in the copending application of Trimmer et al. may be fabricated utilizing rather straightforward stylette designs, obviating the more elaborate mechanical acoustic interface configuration set forth in that application, but still avoiding any substantial contact, and sonic energy transfer, between the conduit/stylette and the surrounding needle.

DESCRIPTION OF THE DRAWINGS

FIGS. 1 through 3 duplicate FIGS. 1 through 3, respectively of the copending Trimmer et al. application, and set forth views of an illustrative embodiment of that invention.

FIGS. 5 and 6 illustrate a preferred embodiment of the principles of the present invention.

BEST MODE FOR CARRYING OUT THE INVENTION

Figure 4A:
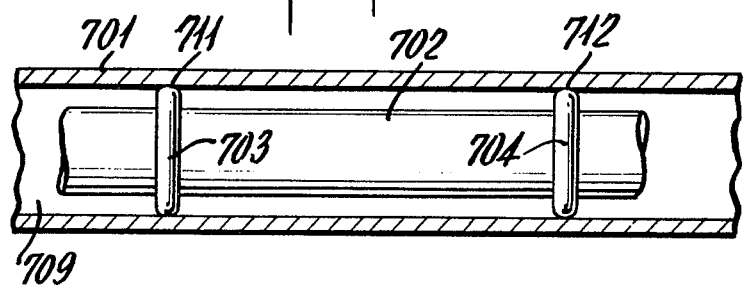
FIGS. 4A through 4D, inclusive, duplicate drawings from the copending Trimmer et al. application which relate to mechanical acoustic insulation of the stylette from the interior of the needle.

Referring first to FIGS. 1 through 3, inclusive, there is shown an illustrative embodiment of the invention described and claimed in the referenced copending, concurrently filed application of Trimmer et al. In those drawings, a needle 101, for example a conventional aspiration biopsy needle, carries therewithin a stylette 102. The stylette 102 terminates in the region of the tip area 106 of the needle 101. In preferred embodiments, the stylette 102 terminates in a matching layer 107 at its extreme end, and is beveled as shown. An annular recess 109 is defined between the stylette 102 and the inner walls of the needle 101. In the embodiment of FIG. 2, an annular "gasket" of flexible material 108 insulates the tipmost region of the stylette 102 from the interior of the needle sheath 101, and prevents circulation of body fluids back up into the annular recess 109 as the needle and stylette are inserted. In accordance with the principles of the present invention, an annular flexible "gasket" 108 is optional, but generally necessary and desirable in view of the packing of the plastic microspheres in the void 109.

Figure 4B:
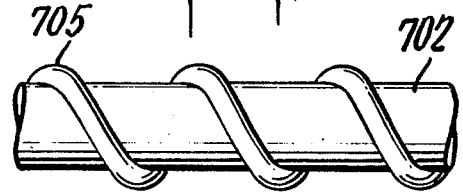
Figure 4C:
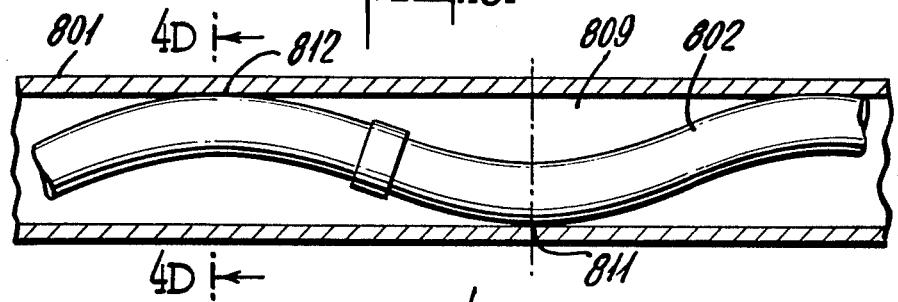
Figure 4D:
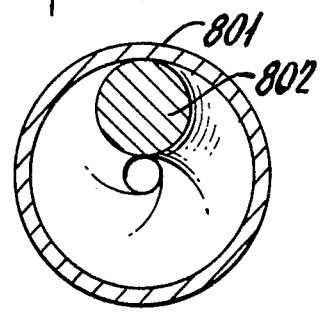

FIGS. 4A through 4D are also duplicates from the copending concurrently filed Trimmer et al. application, and show various mechanical approaches to the acoustic insulation of the stylette from the interior of the needle sheath. In FIG. 4A, periodic annular raised portions 703, 704, etc. extend outwardly from the stylette 702, making occasional, substantially point contacts 711, 712, etc., within the interior of the needle 701, thereby maintaining an air gap 709 between the stylette 702 and the needle 701. In FIG. 4B, a similar approach is followed, except that a helical raised portion 705 is employed. In FIG. 4C, shown in cross section in FIG. 4D, a winding, helically shaped stylette 802 is carried within the needle 801, thereby faking occasional, substantially point contacts at 811, 812, etc. and forming the void 809 thereabout.

It will be noted that each of the mechanical insulation schemes of FIGS. 4A through 4D, inclusive, being restricted to very short, essentially point contacts and/or very oblique angles of contact which are transverse to the stylette axis, serve substantially to convey the acoustic pressure wave up the stylette/conduit. Nevertheless, some contact is thereby entailed, and it is possible that some of the sonic energy will be distributed to the needle, and hence lost for detection purposes. In any event, each of the designs shown in FIGS. 4A through 4D, inclusive, entails fairly formidable manufacturing requirements, tolerances, and costs, thereby diminishing the economic goals to which the Trimmer et al. invention is in part addressed.

Referring, then, to FIGS. 5 and 6, there is shown a preferred embodiment of the principles of the present invention. In particular, FIG. 5 shows a partial lateral cutaway of the embodiment, whereas FIG. 6 shows only the distal end of the apparatus, which is inserted into the body. In particular, a tubular sheath 501, for example a stainless steel aspiration needle having an inside diameter in the range of one-half millimeters or less, has a proximal end which is grasped in conventional fashion for insertion into the body, and a distal end 509 beveled at some angle, for example 45°, as taught in the copending Trimmer et al. application. Within the needle 501 is a rod-like, generally coaxial stylette (i.e. sonic conduit) 502 which terminates at a surface 507 in the region of the distal end 509 of the needle 501. As taught in the copending concurrently filed application of Trimmer et al., the distal surface 507 of the stylette 502 may be simply of polished metal, or may include a matching layer such as that shown in FIG. 2.

The stylette 502 optionally carries a collar or "stop" 510 which limits its travel within the needle 501, and hence also establishes preferred positions for the distal end 507 of the stylette 502. At its extreme proximal end, the stylette 502 defines a broader portion 505 for coupling to a transducer apparatus, as is taught by Trimmer et al.

In accordance with the principles of the present invention, the space intermediate the stylette 502 and the inner surface of the needle 501 is filled with hollow, plastic microspheres, which provide acoustic insulation of the stylette from its surrounding needle 501. In preferred embodiments, these hollow plastic microspheres, having an approximate diameter of 0.8 millimeters, substantially completely pack the space between the stylette 502 and the needle 501.

A preferred fashion for assembling the embodiment of FIGS. 5 and 6 is as follows. The stylette, which preferably is formed of stainless steel material, is provided with a coating of a film of low viscosity, nonconductive epoxy, for example in the range of 0.005 millimeters in thickness. This may be done in conventional fashion either by dip coating or spin coating the epoxy onto the stylette. Thereupon, the coated stylette is dipped into a vessel which contains the loose, hollow plastic microspheres. These then adhere to the epoxy, in fact in quite permanent fashion upon curing thereof. This process may be repeated a number of times, as desired, with the epoxy being allowed fully to cure with the plastic microspheres adherent thereon. Then, the coated stylette is carefully inserted either into the needle directly, or into a tube which conforms to the size of the needle into which the stylette will be applied. Excess microspheres thereby are sheared from the aggregate on the stylette, and there results a well-formed stylette 502 coated with microspheres 511 which may be inserted for use (e.g., see FIG. 6) in accordance with the methods taught in the copending Trimmer et al. application. It will be noted that the excellent acoustic insulation achieved in accordance with the principles of the present invention allows for improved transmission, as well as reception capacity. That is, in accordance with the principles of the present invention, sonic energy coupled to the stylette at 505 will be carried with very low degrees of energy loss down through the stylette 502, and emitted into the surrounding tissue via the distal surface 507 of the stylette 502.

In a preferred embodiment, the epoxy used to bond the microspheres to the stylette is that commercially available from Tra-Con, Inc. under the trade designation Tra-Bond 2113 ®, which, as is known in the art, is a clear, low viscosity epoxy adhesive. In such preferred embodiment, the microspheres are those commercially available and generally known as microballoons, for example those sold by Emerson & Cuming, Inc. under the trade designation Eccospheres ®, which have a size tolerance of ±20%.

We claim:

1. In an ultrasound needle tip locator system employing an imaging transducer external to the body, hollow needle means for insertion into the body, and conduit means carried within said needle means for detecting sonic energy at the needle means tip and for conveying sonic energy through the needle means and outside the body, and means for acoustic insulation of said conduit means from the inner surface of said needle means, the improvement wherein said means for insulation comprises a packing of microspheres in the void between said conduit means and the inner surface of said needle means.

2. A system means as described in claim 1 wherein said microspheres are hollow, composed of plastic material, and sized in the range less than 0.1 mm. diameter.

3. A system means as described in claim 2 wherein said conduit means is composed of solid, sonically conductive material, and said microspheres are bonded to said conduit means and to one another by low viscosity, sonically nonconductive epoxy.

* * * * *